United States Patent [19]
Bormann et al.

[11] 4,282,220
[45] Aug. 4, 1981

[54] CEPHEM DERIVATIVES

[75] Inventors: Dieter Bormann, Kelkheim; Walter Dürckheimer, Hattersheim; Elmar Schrinner, Wiesbaden, all of Fed. Rep. of Germany

[73] Assignee: Hoechst Aktiengesellschaft, Frankfurt am Main, Fed. Rep. of Germany

[21] Appl. No.: 42,066

[22] Filed: May 24, 1979

[30] Foreign Application Priority Data

May 26, 1978 [DE] Fed. Rep. of Germany ....... 2822860

[51] Int. Cl.³ ............................................. C07D 501/20
[52] U.S. Cl. ..................................... 424/246; 544/28; 544/21
[58] Field of Search ....................... 544/28, 21, 27, 22; 424/246

[56] References Cited

U.S. PATENT DOCUMENTS 4,152,432  5/1979  Heymes .................................. 544/27
4,166,115  8/1979  Takaya et al. ......................... 544/26

OTHER PUBLICATIONS

Hackh's Chemical Dictionary, pp. 248 and 595, (1969).

Primary Examiner—Nicholas S. Rizzo
Attorney, Agent, or Firm—Curtis, Morris & Safford

[57] ABSTRACT

What is disclosed are cephalosporin compounds of the formula

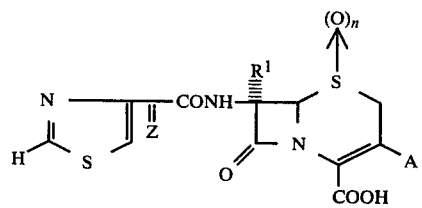

pharmaceutical preparations having an action against bacterial infections and containing such cephem compounds, a process for the manufacture of the cephem compounds and of pharmaceutical preparations containing the same, and the use of the cephem compounds to combat bacterial infections.

7 Claims, No Drawings

CEPHEM DERIVATIVES

This invention relates to cephem compounds of the formula I

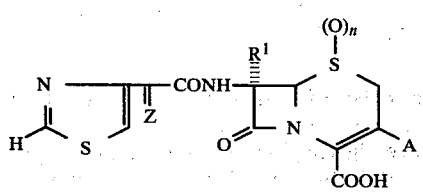

in which n denotes zero or 1, A denotes methyl or —CH$_2$O— acyl with low molecular weight acyl, Z denotes oxygen or =NOR in which R is hydrogen, saturated or unsaturated lower alkyl or a protective group and R$_1$ denotes hydrogen or lower alkoxy, and the pharmacologically acceptable salts and esters thereof.

The invention furthermore relates to a process for the manufacture of compounds of formula I, which comprises reacting a cephem compound of the formula II or an ester thereof

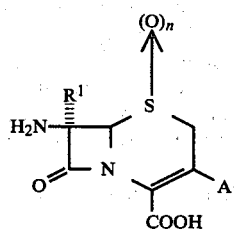

in which A, n and R$^1$ are as defined above, with a thiazolyl carboxylic acid of the formula III

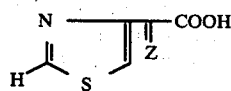

in which Z is as defined above, in the form of its activated derivative capable of amide formation, or oxidizing a compound of the formula I in which n is zero to obtain a compound of the formula I in which n is 1 and, in the case of Z having the meaning of =NOR, optionally splitting off the radical R if it denotes a protective group.

It is still another object of the present invention to provide compounds of the formula III, their esters and salts and processes for the manufacture of these compounds, which comprises halogenating (a) an acetyl-glyoxyl ester, subsequently subjecting the product obtained to cyclization with thioformamide to give the thiazol-4-yl glyoxyl ester of the formula III in which E denotes any radical of an alcohol, and saponifying the ester obtained in an alkaline or acid medium to obtain the thiazol-4-yl glyocylic acid

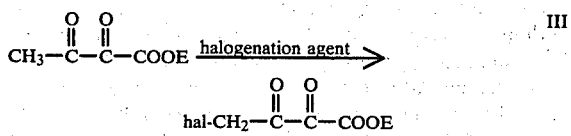

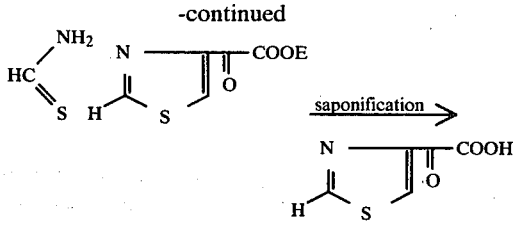

(b) halogenating an acetoacetic ester, subjecting the product obtained to cyclization with thioformamide to give the thiazol-4-yl acetic acid ethyl ester, and oxidizing the latter to obtain the thiazol-4-yl glyoxyl ester of the formula III

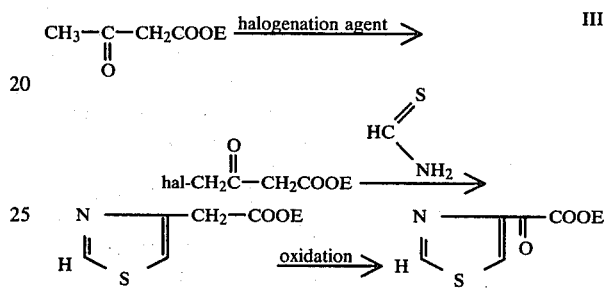

(c) reacting thiazol-4-yl glyoxylic acid or an ester thereof with hydroxyl amine to obtain a compound of the formula II in which Z denotes =NOH and optionally saponifying the ester;

(d) converting 2-(thiazol-4-yl)-2-hydroxyiminoacetic acid or an ester thereof with an alkylation agent into a compound of the formula III in which Z denotes =NOR; or (e) reacting thiazol-4-yl glyoxylic acid or an ester thereof with a hydroxyamine compound of the formula N$_2$H—OR and optionally saponifying the ester obtained; or (f) oxidizing an ω-haloacetic acid ester and reacting the haloacetoglyoxyl ester with thioformamide

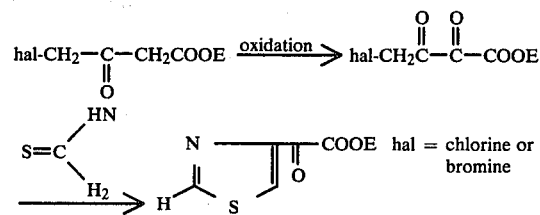

(g) converting a 2-aminothiazol-carboxylic acid of the formula

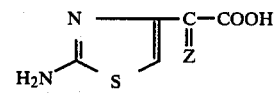

or an ester thereof, in situ and in known manner, into a 2-diazonium salt and reducing the latter by means of a reducing agent, preferably hypophosphorous acid, in the presence of pulverulent Cu; or (h) converting a 2-aminothiazol-carboxylic acid of the formula

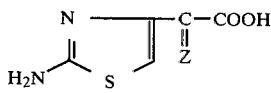

or an ester thereof by a Sandmeyer reaction in a 2-bromothiazol derivative and dehalogenating the latter with catalytically excited hydrogen.

As pharmacologically acceptable salts of the cephem compounds of formula I, inorganic and organic salts come into consideration, preferably the alkali metal and alkaline earth metal salts and more preferably the sodium, magnesium and calcium salts, the triethyl ammonium salt or the procaine salt.

As pharmacologically acceptable esters, there are especially mentioned those esters which can readily cleaved for example the acetoxymethyl esters, pivaloylmethyl esters and the phthalide ester.

In case Z in formula I is =NRO, suitable radicals R are hydrogen or lower alkyl having from 1 to 5 carbon atoms, preferably 1 to 3 carbon atoms, which can be either saturated or unsaturated, such as methyl, ethyl, allyl, vinyl, propyl, isopropyl, butyl, isobutyl, or pentenyl, preferably methyl, ethyl and allyl. Hydrogen and methyl are especially preferred as the radical R.

In case $R^1$ in formula I is lower alkoxy, radicals having from 1 to 4 carbon atoms are suitable, such as methoxy, ethoxy and preferably methoxy. If A in formula I denotes —$CH_2O$-acyl, acyl preferably has from 1 to 5 carbon atoms, for example formyl, acetyl or propionyl and preferably acetyl.

The cephem compounds of the formula

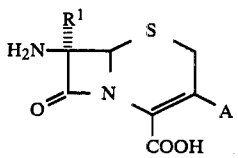

and their esters in which A and $R^1$ are as defined above, to be used in the reactions according to the invention, are known in the literature.

The starting compounds of the formula

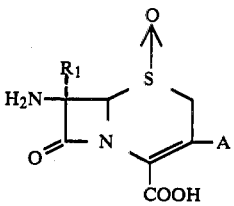

can be obtained by oxidation of the corresponding 7-aminocephalosporanic acid derivatives in the manner described below.

The carboxylic acids of formula III used for acylation are novel and can be prepared according to the invention in good yields. Method (a) uses as the starting compound the acetylglyoxyl ester, which can be prepared from acetoacetic ester according to methods described in the literature.

For the formation of the thiazol ring, several procedures have been described in the literature, for example the reaction of chloroketo derivatives with thioformamide according to the following equation

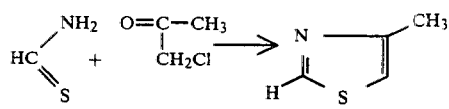

It has now been found, surprisingly, that the acetylglyoxylic acid esters can be converted into halogenoacetylglyoxyl esters in a smooth manner and with high yields. Suitable halogenation agents are especially sulfuryl chloride and elemental bromine.

The halogenation is carried out in a solvent. Suitable solvents are preferably halogenated hydrocarbons, for example methylene chloride, chloroform and ethylene dichloride.

The reaction can be carried out in a wide temperature range. To obtain high yields of monohalogenoacetylglyoxyl ester, a temperature range from −20° C. to +20° C. is preferred.

When elemental bromine is used for the halogenation, the crude bromoacetylglyoxyl ester can be directly reacted further with thioformamide.

Alternatively, the bromo- and chloroacetylglyoxyl ester can be obtained by oxidation of ω-bromo- or ω-chloroacetoacetic ester (method f). An especially suitable oxidant is selenium dioxide, which is used in a halogenated hydrocarbon forming an azeotrope with water, for example chloroform and ethylene dichloride. After separation from the crude selenium, the desired product is obtained in a high yield. It can be reacted with thioformamide either directly or, if desired, after distillation.

To obtain good yields the thioformamide should be used in an at least equimolar amount. Care should be taken that the thioformamide is freshly prepared by a method known in the literature.

The reaction can be carried out in various ways. According to a preferred method, the halogen compound is added to the solution of the freshly prepared thioformamide.

Suitable solvents for this reaction are various organic solvents, for example alcohols as well as mixtures of organic solvents with water, for example of alcohol and water, preferably a mixture of ethanol and water. The reaction is preferably carried out in ethanol.

The reaction can be carried out in a wide temperature range, for example from −50° C. to +80° C., preferably −20° C. to +30° C. The final products are isolated in known manner, for example by extraction of the reaction product with subsequent distillation.

The 1,3-thiazol-4-yl-glyoxylic acid esters purified by distillation are saponified in known manner to obtain the 1,3-thiazol-4-yl-glyoxylic acid, for example with aqueous alkali metal or alkaline earth metal hydroxides, for example sodium hydroxide solution. The esters as well as the acids are valuable starting compounds for the manufacture of compounds of the formula III in which Z denotes =NOR, as illustrated in methods (c), (d) and (e).

The 1,3-thiazol-4-yl acetic acid ethyl ester used in method (b) is known in the literature. The oxidation of the acetic acid grouping to the corresponding glyoxylic acid grouping takes place in an especially smooth manner and in a good yield if it is carried out in an inert organic solvent capable of removing the water formed in the oxidation in the form of an azeotrope. Suitable solvents of this type are benzene and halogenated hydrocarbons, preferably dichloroethylene.

Oxidation is brought about by adding an oxidant. The oxidation is especially simple with the use of selenium dioxide at the boiling point of the azeotrope forming.

The progress of the oxidation can be followed in simple manner by the splitting off of water. For further working up, the reaction mixture can be filtered and subjected to fractional distillation.

The 1,3-thiazol-4-yl glyoxyl esters obtained by methods (a), (b) or (f) can be converted into the 1,3-thiazol-4-yl glycoxylic acids by simple saponification, which acids, after appropriate activation, can be reacted with the cephem compounds of formula II. For activation a great number of reagents can be used. The formation of a symmetrical or asymmetrical anhydride takes place in an especially simple manner in a solvent that is inert to the reaction mixture, preferably a halogenated hydrocarbon, for example methylene chloride or chloroform, in a wide temperature range.

According to a preferred mode of activation, the 1,3-thiazol-4-yl glyoxylic acid is reacted with a chloroformic acid ester or pivaloylic acid chloride and converted into a salt. It has been found that the reaction takes a smooth course when the acid is suspended in a halogenated hydrocarbon, for example methylene chloride, and converted into the triethylammonium salt by an organic base, for example triethyl amine. Alternatively, the alkali metal salt of 1,3-thiazol-4-yl glyoxylic acid can be used. In this case, the addition of catalytic amounts of a tertiary base, for example N,N-dimethylaniline, proved to be favorable.

It is likewise possible to form the inner anhydride of 1,3-thiazol-4-yl glyoxylic acid with the aid of condensing agents, for example dicyclohexyl-carbodiimide, which anhydride is then reacted with an amino-cephemcarboxylic acid derivative of formula II.

The acylation of the cephem compounds of formula II with the 1,3-thiazol-4-yl glyoxylic acid derivatives can be carried out under different experimental conditions. The amino-cephem derivatives of formula II can be acylated in the most different solvents. As solvents, organic solvents such as halogenated hydrocarbons, for example methylene chloride, or chloroform, or tertiary amides, for example dimethyl formamide or dimethyl acetamide can be used.

For a good performance of the reaction it is desirable to dissolve the amino-lactam derivative of formula II.

In the case of aminocephem esters of the formula II, the reaction is carried out in organic solvents in which most esters are well soluble. Suitable solvents are, for example, halogenated hydrocarbons or tertiary amides.

Suitable esters in the sense of the invention are, for example, compounds of formula II in which the ester group is a phthalide ester or an ester of lower alkyl, preferably tertiary butyl or substituted methyl. Preferred substituents on methyl are trichloromethyl, acyloxy (preferably acetoxy or pivalolyloxy), or one or two phenyl radicals which, on their part, can be substituted, for example by lower alkoxy (preferably methoxy) or by the nitro group. Preferred examples of the aforesaid definitions are the tert.-butyl, trichloroethyl, p-methoxybenzyl, benzhydryl, acetoxymethyl, and pivaloyloxymethyl esters, or the phthalide esters.

With the use of amino-cephem carboxylic acid of the formula II, the compounds must be dissolved, preferably with the addition of bases or by silylation. Suitable silylation agents are all conventional reagents of this type, preferably trimethylsilane, which is used in the presence of a stoichiometric amount of a base, more preferably, however, O,N-bistrimethylsilyl acetamide, which can be used without the addition of a base is used. To obtain satisfactory yields, the silylation agent should be used in a proportion of approximately 2 equivalents of silyl for each mol of amino-cephem compound of formula II.

For the dissolution of the 7-ACS and a great number of 7-amino-$\Delta^3$-cephem-4-carboxylic acids, organic bases are especially useful. For the preparation of solutions in organic solvents, tertiary amines, such as triethyl amine, N,N-dimethyl aniline and N-methylmorpholine, proved to be particularly suitable.

In general, the bases are added in an at least stoichiometric amount, calculated on the desired reaction. It is recommended, however, to use an excess of base, for example of about 20 to 80%.

When compounds of formula II that are sensitive to bases are dissolved, a pH of about 4 to 8, preferably 6 to 7, can be kept constant by a continuous addition of the base.

The amino-lactam derivatives of formula II can be dissolved in a wide temperature range. In the case of derivatives sensitive to bases, it is recommended, however, to operate in a temperature range of from about 0° to 15° C.

The activated 1,3-thiazol-4-yl glyoxylic acid is added to the dissolved or possibly suspended amino-cephem derivative of formula II. The reaction is carried out in known manner at a temperature as used for the manufacture of carboxylic acid amides from reactive carboxylic acid derivatives of formula III. A temperature range of from $-50°$ to $+30°$ C. and preferably from $-20°$ to $0°$ C., proved to be suitable.

In order to obtain a high yield, the activated acid derivative of formula III is used in an at least stoichiometric amount. An excess of 5 to 25% may prove advantageous.

The acylation products can be isolated in a known manner. For example the acid derivative of formula I, optionally after evaporation of the organic solvent, can be taken up in water and precipitated by the addition of a mineral acid. Suitable mineral acids are, in the first place, dilute acids such as hydrochloric acid or sulfuric acid. In most cases the amido-cephem acids of formula I are obtained in the form of amorphous solids or crystals. They can be isolated as free acids by extraction at pH 2 to 1. For extraction various organic solvents immiscible with water can be used, for example halogenated, hydrocarbons such as methylene chloride, or esters, for example acetic acid ethyl ester or acetic acid n-butyl ester, and also ketones such as methylisobutyl ketone.

The amido-cephem acids of the formula I are obtained from the extracts, for example by evaporation of the solvent and rubbing, for example with ether.

The reaction described sub (g) can be carried out, for example, by diazotizing the corresponding 2-aminothiazolcarboxylic acids or the esters thereof in acid solution, while cooling and adding sodium nitrite solution, and reducing the diazonium salt formed as an intermediate in a manner known for the reduction of diazonium salts, for example by using hypophosphorous acid. In the case of the esters, the neutralized solution can then be extracted for isolation. The free acids can be obtained, for example, by alkaline saponification of the extract.

When working according to method (h), the diazonium compound can be converted into the corresponding bromine compound by a treatment with hydrobromic acid and pulverulent copper, which bromine compound is then dehalogenated quantitatively by catalytically excited hydrogen, for example by reduction in the presence of Raney nickel and a base.

The 1,3-thiazol-4-yl glyoxylic acid esters and the corresponding carboxylic acid derivatives prepared by methods (a), (b) or (f) can be converted by methods (c), (d) and (e) into compounds of formula III in which Z denotes the group NOR—.

To carry out this reaction, the 1,3-thiazol-4-yl glyoxylic acid ester or the corresponding carboxylic acid is reacted with hydroxyl amine (method c) or with a hydroxylamine-O-alkyl or hydroxylamine-O-aryl derivative (method e). The hydroxyl amine derivatives of the formula H₂NOR in which R has the aforesaid meaning are described in the literature and can be prepared in simple manner by the processes as indicated. The hydroxyl amine or hydroxyl amine derivatives of the formula H₂NOR are reacted with the 1,3-thiazol-4-yl glyoxylic acid or ester thereof in a manner known in the literature, for example as described in "Organicum", VEB Deutscher Verlag der Wissenschaften, 1967, pages 369 et seq. for the reaction of carbonyl groups with carbonyl reagents. The 2-(1,3-thiazol-4-yl)-2-oximino-acetic acid obtained in this reaction contains the oxime grouping in syn-position with respect to the COOH group as represented by the formula VI.

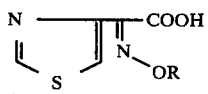

VI

When in the compound of formula VI R denotes hydrogen, it can be alkylated in a simple manner and with a high yield in the presence of organic or inorganic bases (method d). Suitable alkylation agents are dialkyl sulfates, for example dimethyl sulfate, as well as alkyl halides, for example methyl iodide, benzyl bromide, p-methoxybenzyl chloride, or triphenylchloromethane. The bases used as auxiliaries for the alkylation can be chosen, in accordance with the type of reaction, from alkali metal and alkaline earth metal hydroxides, for example sodium or potassium hydroxide, and the organic bases, for example triethyl amine. The alkylation is carried out in a solvent or solvent mixture. The use of water or of mixtures of alcohol and water or of halogenated hydrocarbons such as methylene chloride or chloroform proved to be especially suitable.

The final products are worked up according to methods known from experience. In the case of esters, these need not be purified but can be directly converted into the free acids.

The 1,3-thiazol-4-yl-acetic acid derivatives of formula III in which X denotes =NOR (with R possibly not being hydrogen) are reacted with the cephem compounds of formula II in known manner as described above, for example, after activation of the carboxylic acid group, by conversion into a grouping capable of amide formation, preferably the conversion into an active ester, for example the hydroxybenztriazole ester, or by conversion into an acid halide, preferably an acid chloride, or by conversion into a symmetrical or asymmetrical anhydride.

Especially mild conditions should be chosen for activation in order to prevent the syn-oximes from transposing into the trans-oximes as illustrated by the following formula

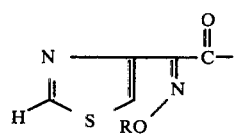

The activation is, therefore, carried out at low temperatures in the range from −50° to +30° C. and preferably −10° to +10° C.

The manufacture of compounds in which the oxime grouping =NOR has the syn-configuration is thus a preferred embodiment of the invention.

When the symmetrical anhydride is used for the reaction, the side chain acid set free in the acylation is separated, for example by extraction or precipitation.

In the manufacture of compounds of formula I in which Z denotes =N—OH, it proved useful to block temporarily the NOH group in the carboxylic acid of formula III by a protective group commonly used for reactions of this type, for example a tetrahydropyranyl group or a triarylmethyl group. Especially good results are obtained with triphenylmethyl as a protective group, which, after isolation of the final products, can be split off again by a method known in the literature, for example with aqueous formic acid. When the N—OH group in the thiazol-4-yl acids of formula III is temporarily blocked, it is recommended to use the esters of formula III, which are subsequently saponified by alkaline hydrolysis to give the carboxylic acids with a protected N—OH group.

Compounds of formula I in which n is 1, i.e. cephem-S-oxides, can also be prepared by oxidation of compounds of formula I in which n is zero.

The oxidation of cephem derivatives at the sulfur atom has been described repeatedly. In this reaction α- and β-oxides can be formed, depending on the oxidant used (cf. E. Flynn Cephalosporins and Penicillins, Chemistry and Biology, Academic Press, 1972, pages 135 et seq.).

β-S-oxides are obtained, for example, with peracetic acid in glacial acetic acid. The reaction temperature is not critical but, for avoiding undesired secondary reactions, the reaction should be carried out at room temperature using an at least stoichiometric amount of oxidant. In many cases an excess of from 10 to 100% proves to be expedient, provided that the reaction temperature is not raised substantially.

The isolation of the cephem-S-oxides obtained in this manner is not difficult, precipitation with subsequent filtration or extraction being possible, for example.

The amidocephem compounds of formula I can be converted into the physiologically acceptable esters of formula I also by subsequent esterification according to processes known in the literature. The acetoxymethyl or pivaloyloxymethyl ester can be obtained, for example, by reacting the alkali metal salts, preferably sodium salts, or ammonium salts, preferably triethyl ammonium salts, with the corresponding halomethylacyl compounds, for example chloromethyl acetate, chloromethyl propionate or pivalic acid chloromethyl ester.

If esters, and particularly if physiologically acceptable esters, are obtained in the acylation reaction, a subsequent esterification of the carboxyl group can be dispensed with.

The esters directly obtained in the reaction according to the invention, for example the p-methoxybenzyl, p-nitrobenzyl, tert.-butyl or benzhydryl ester, can also be converted into the free carboxylic acids of formula I by methods known in the literature.

The cephem derivatives of formula I are valuable antibiotics which are surprisingly well suited for combating Gram-positive and in particular Gram-negative infections and, moreover, also have an unexpectedly good action against penicillinase-forming staphylococcae.

The compounds according to the invention can be employed as such or together with the auxiliaries and additives customarily used therapeutically, such as tragacanth, lactose, talc, solvents and the like. They can be used in the form of galenic formulations, such as tablets, dragees, capsules, suspensions, solutions and the like. They can be administered perorally or preferably parenterally, and, as a rule, an administration unit contains the active compound in an amount of about 50 to 1,000 mg, preferably about 100 to 500 mg.

For parenteral administration, the solvents known for therapeutic use, especially a solution in water, can be used.

It is also possible to combine the compounds according to the invention with other active compounds. Thus, for example, other antibiotics can be administered, for example those from the series comprising the penicillins, cephalosporins, or compounds which influence the symptoms of bacterial infections, such as antipyretic agents, antiphlogistic agents or analgetics.

In addition to the cephem derivatives of formula I described in the examples, the following compounds can be prepared by the process of the invention:

7-(2-(1,3-thiazol-4-yl)-2-syn-methoximinoacetamido)-3-methyl-Δ3-cephem-4-carboxylic acid,
7-(2-(1,3-thiazol-4-yl)-2-syn-allyloximinoacetamido)-3-methyl-Δ3-cephem-4-carboxylic acid,
7-(2-(1,3-thiazol-4-yl)-2-syn-ethoximinoacetamido)-3-methyl-Δ3-cephem-4-carboxylic acid,
7-((1,3-thiazol-4-yl)-glyoxylamido)-3-methyl-Δ3-cephem-4-carboxylic acid,
7-(2-(1,3-thiazol-4-yl)-2-syn-ethoximinoacetamido)-cephalosporanic acid,
7-(2-(1,3-thiazol-4-yl)-2-syn-propoximinoacetamido)-cephalosporanic acid,
7-(2-(1,3-thiazol-4-yl)-2-syn-butoximino-acetamido)-cephalosporanic acid,
7-(2-(1,3-thiazol-4-yl)-2-syn-pentyloximinoacetamido)-cephalosporanic acid,
7-(2-(1,3-thiazol-4-yl)-2-syn-allyloximinoacetamido)-cephalosporanic acid,
7-(2-(1,3-thiazol-4-yl)-2-syn-allyloximinoacetamido)-cephalosporanic acid β-S-oxide,
7-(2-(1,3-thiazol-4-yl)-2-syn-ethoximinoacetamido)-cephalosporanic acid β-S-oxide,
7-(2-(1,3-thiazol-4-yl)-2-syn-pentyloximinoacetamido)-cephalosporanic acid β-S-oxide,
7-(2-(1,3-thiazol-4-yl)-2-syn-hydroximinoacetamido)-cephalosporanic acid β-S-oxide,
7-(2-(1,3-thiazol-4-yl)-2-syn-i-propyloximinoacetamido)cephalosporanic acid,
7-methoxy-7-(2-(1,3-thiazol-4-yl)-2-syn-methoximinoacetamido)-cephalosporanic acid,
7-methoxy-7-(2-(1,3-thiazol-4-yl)-2-syn-hydroximinoacetamido)-cephalosporanic acid,
7-methoxy-7-(2-(1,3-thiazol-4-yl)-2-syn-pentyloximinoacetamido)-cephalosporanic acid,
7-methoxy-7-(1,3-thiazol-4-yl)-glyoxylamido)-cephalosporanic acid,
7-methoxy-7-(1,3-thiazol-4-yl)-glyoxylamido)-cephalosporanic acid β-S-oxide,
7-methoxy-7-(2-(1,3-thiazol-4-yl)-2-syn-methoximinoacetamido)-cephalosporanic acid β-S-oxide,
7-methoxy-7-(2-(1,3-thiazol-4-yl)-2-syn-methoxyiminoacetamido)-3-methyl-Δ3-cephem-4-carboxylic acid β-S-oxide,
7-methoxy-7-(2-(1,3-thiazol-4-yl)-2-syn-hydroxyiminoacetamido)-3-methyl-Δ3-cephem-4-carboxylic acid β-S-oxide,
7-(2-(1,3-thiazol-4-yl)-2-syn-methoximinoacetamido)-cephalosporanic acid α-S-oxide,
7-(2-(1,3-thiazol-4-yl)-2-syn-hydroximinoacetamido)-3-methyl-Δ3-cephem-4-carboxylic acid β-S-oxide,
7-(2-(1,3-thiazol-4-yl)-2-syn-hydroximinoacetamido)-3-methyl-Δ3-cephem-4-carboxylic acid α-S-oxide,
7-(2-(1,3-thiazol-4-yl)-2-syn-ethoximinoacetamido)-3-methyl-Δ3-cephem-4-carboxylic acid β-S-oxide,
7-methoxy-7-(2-(1,3-thiazol-4-yl)-2-syn-ethoximinoacetamido)-cephalosporaic acid,
7-methoxy-7-(2-(1,3-thiazol-4-yl)-2-syn-ethoximinoacetamido)-cephalosporanic acid β-S-oxide,
7-(2-(1,3-thiazol-4-yl)-2-syn-propoximinoacetamido)-3-methyl-Δ3-cephem-4-carboxylic acid,
7-methoxy-7-(2-(1,3-thiazol-4-yl)-2-syn-propoximinoacetamido)-3-methyl-Δ3-cephem-4-carboxylic acid,
7-methoxy-7-(2-(1,3-thiazol-4-yl)-2-syn-propoximinoacetamido)-cephalosporanic acid,
7-methoxy-7-(2-(1,3-thiazol-4-yl)-2-syn-allyloximinoacetamido)-cephalosporanic acid,
7-methoxy-7-(2-(1,3-thiazol-4-yl)-2-syn-allyloximinoacetamido)-cephalosporanic acid β-S-oxide.

These compounds, too, can be used as such or after conversion into their salts, especially the sodium, calcium or magnesium salts, or as esters, especially the acetoxymethyl or pivaloyloxymethyl esters.

The following examples illustrate the invention but they are not intended to limit it thereto.

EXAMPLE 1

7-(2-(1,3-Thiazol-4-yl)-2-syn-methoximino-acetamido)-cephalosporanic acid

With the exclusion of moisture, a solution of 1.58 g of dicyclohexyl carbodiimide in 10 ml of methylene chloride is added dropwise at 0° C. to a suspension of 2.6 g of 2-(1,3-thiazol-4-yl)-2-syn-methoximino-acetic acid in 50 ml of methylene chloride. The reaction mixture is kept for 2 hours at 0° C., then cooled to −5° C. and a solution of 1.9 g of 7-aminocephalosporanic acid in 25 ml of methylene chloride and 1.5 g of triethyl amine are added. The mixture is stirred for 3 hours without cooling and filtered to remove the urea formed.

The filtrate is evaporated to dryness, the residue is taken up in a small volume of water, a pH of 4 is adjusted and unreacted 7-ACS is separated.

The mother liquor is acidified to pH 1 with 2 N HCl, well cooled and the precipitated crystal magma is isolated. After drying, a small volume of methanol is added to the mixture of 2-(1,3-thiazol-4-yl)-2-syn-metoximino-acetic acid and the desired 7-(2-(1,3-thiazol-4-yl)-2-synmethoximino-acetamido)-cephalosporanic acid and the mixture is well cooled, whereupon the cephem compound crystallizes in the form of almost colorless crystals. The crystals are isolated and washed with a small amount of cold methanol, whereupon the 7-(2-(1,3-thiazol-4-yl)-2-syn-methoximinoacetamido)-cephalosporanic acid melting at 140° to 142° C. with decomposition is obtained in the form of almost colorless crystals.

Thin layer chromatogram (butanol:H$_2$O:ethanol:glacial acetic acid=5:2:1.5:1.5).

Rf=0.43; IR in KBr: lactam —CO 1750 cm$^{-1}$.

NMR: thiazol protons at $\alpha$=7.93 and 9.13 ppm (measured in (CD$_3$)$_2$SO), each time doublet J=2 c.p.s.

EXAMPLE 2

7-(2-(1,3-Thiazol-4-yl)-2-syn-methoximino-acetamido)-cephalosporanic acid

With the exclusion of moisture, 3.6 ml of dimethyl acetamide are added at −10° C. to a suspension of 7.4 g of 2-(1,3-thiazol-4-yl)-2-syn-methoximino-acetic acid in 75 ml of methylene chloride and then 25 ml of a 21.3% phosgene solution in toluene are added dropwise at −10° C. over a period of 15 minutes. The reaction mixture is stirred for 2 hours whereby the 2-(1,3-thiazol-4-yl)-2-syn-methoximinoacetic acid chloride forms. Next, a solution of 10.85 g of 7-aminocephalosporanic acid in 200 ml of methylene chloride, 10.3 ml of triethyl amine and 6.8 of pyrrolidone are added dropwise at −10° C. The reaction mixture is stirred for 2 hours at −5° C., water is added to the organic phase, the pH is adjusted to 7 and then the aqueous phase is separated. The pH of the aqueous phase is adjusted to 3.5. It is filtered and then acidified to pH 1. The precipitated crystals are isolated by extraction with ethyl acetate. The ethyl acetate phase is dried, concentrated, and the residue is dissolved in a small amount of methanol. On cooling, the 7-(2-(1,3-thiazol-4-yl)-2-syn-methoximinoacetamido)-cephalosporanic acid separates in the form of colorless crystals meltings at 140° to 142° C.

EXAMPLE 3

7-(2-(1,3-Thiazol-4-yl)-2-syn-triphenylmethoximino-acetamido)-cephalosporanic acid 2.9 g of 2-(1,3-thiazol-4-yl)-2-syn-triphenylmethoximino-acetic acid are severely dried in high vacuum. 40 ml of toluene and 0.54 ml of dimethyl formamide are added, the reaction mixture is cooled to −10° C. and 5 ml of 32% phosgene solution in toluene are added. After 2.5 hours at −10° C., a solution of 1.9 g of 7-amino-cephalosporanic acid in 30 ml of methylene chloride and 4 ml of triethyl amine are added dropwise. Stirring is continued for 2 hours, towards the end without cooling bath so that the temperature rises to +20° C., and finally 60 ml of iced water are added. The organic phase is separated and the aqueous phase is washed once more with methylene chloride. The combined organic phases are dried over Na$_2$SO$_4$ and filtered. The solvent is removed and the residue is rubbed with ether. A solid is isolated which is washed with ether and dried. 7-(2-(1,3-Thiazol-4-yl)-2-syn-triphenylmethoximinoacetamido)-cephalosporanic acid melting at 135° to 140° C. with decomposition is obtained.

TLC (eluant as in Example 1): Rf 0.71; IR in KBr: Lactam CO: 1780 cm$^{-1}$.

EXAMPLE 4

7-(2-(1,3-Thiazol-4-yl)-2-syn-hydroximino-acetamido)-cephalosporanic acid 2.03 g of 7-(2-(1,3-thiazol-4-yl)-2-syn-triphenylmethoximino-acetamido)-cephalosporanic acid prepared as described in Example 3 are added to a mixture of 20 ml of 100% formic acid and 5 ml of water, the mixture is stirred for 2 hours at room temperature and the precipitated triphenyl carbinol is removed by filtration. The filtrate is concentrated to dryness, 20 ml of ether and 20 ml of isopropanol are added to the residue and the whole is triturated. A solid is formed which is isolated, washed with ether and dried. 7-(2-(1,3-thiazol-4-yl)-2-syn-hydroximino-acetamido-cephalosporanic acid is obtained in the form of a cream-colored solid which does not melt at a temperature up to 250° C. TLC (eluant ethyl acetate:ethanol:H$_2$O:HCOOH 60:25:15:1): Rf 0.57, IR in KBr: lactam CO 1770 cm$^{-1}$, NMR ((CD$_3$)$_2$SO): thiazol protons $\delta$=7.81 and 9.08 ppm, each time doublet J=1.5 c.p.s.

EXAMPLE 5

7-(2-(1,3-Thiazol-4-yl)-glyoxylamido)-cephalosporanic acid

With the exclusion of moisture; a solution of 2.5 g of pivalic acid chloride in 10 ml of methylene chloride is added at 0° C. to a solution of 3.14 g of 1,3-thiazol-4-yl glyoxylic acid in 30 ml of methylene chloride and 2.2 g of triethylamine and the mixture is stirred for 1 hour. Next, a solution of 5.44 g of 7-aminocephalosporanic acid in 30 ml of methylene chloride and 6.06 g of triethyl amine are added dropwise to the reaction mixture. The whole is stirred for 30 minutes at 0° C. and then for 2 hours at room temperature, whereupon the solvent is removed.

The residue is taken up in 100 ml of water and a pH of 3.5 is adjusted to separate 7-aminocephalosporanic acid, if any, the mixture is filtered. The pH is adjusted to 1 and the precipitated crystals are isolated. 7-(2-(1,3-Thiazol-4-yl)-glyoxylamido)-cephalosporanic acid is obtained in the form of a beige solid.

TLC (butanol:water:ethanol:glacial acetic acid 5:2:1.5:1.5) Rf 0.38, lactam CO 1772 cm$^{-1}$.

A further amount of this compound can be obtained in the form of a cream-colored solid by extraction with ethyl acetate and subsequent trituration with ether.

NMR ((CD$_3$)$_2$SO)-thiazol protons at 8.85 and 9.23 ppm, each time doublets J=2 c.p.s.

EXAMPLE 6

7-(2-(1,3-Thiazol-4-yl)-2-syn-methoximino-acetamido)-cephalosporanic acid $\beta$-S-oxide A solution of 800 mg of 40% peracetic acid in glacial acetic acid is added at room temperature to a suspension of 1 g of 7-(2-(1,3-thiazol-4-yl)-2-syn-methoximino-acetamido)cephalosporanic acid, prepared as described in Example 1, in 10 ml of 80% acetic acid. Stirring of the reaction mixture is continued for 30 minutes at room temperature and the precipitated crystals are isolated and washed with methanol and ether. 7-(2-(1,3-Thiazol-4-yl)-2-syn-methoximino-acetamido)-cephalosporanic acid $\beta$-S-oxide is isolated in the form of colorless crystals melting at 175° to 176° C. with decomposition.

TLC (eluant butanol:H$_2$O:C$_2$H$_5$OH:CH$_3$COOH 5:2:1.5:1.5 Rf 0.29, IR in KBr: lactam CO at 1785 cm$^{-1}$, NMR: thiazol protons at δ 7.96 and 9.13 ppm ((CD$_3$)$_2$SO), each time doublets J=2 c.p.s.

EXAMPLE 7

7-(2-(1,3-Thiazol-4-yl)-glyoxylamido)-cephalosporanic acid β-S-oxide 1 g of 40% peracetic acid in glacial acetic acid is added, while slightly cooling, to a solution of 1.5 g of 7-(1,3-thiazol-4-yl-glyoxylamido)-cephalosporanic acid, prepared as decribed in Example 5, in 25 ml of 80% glacial acetic acid, at a rate such that the temperature does not exceed 25° C.

After 30 minutes, 10 ml of methanol are added to the reaction mixture, which is then concentrated to dryness under reduced pressure. After rubbing with ether, the residue yields an amorphous solid which is isolated and repeatedly washed with ether. 7-(2-(1,3-Thiazol-4-yl)-glyoxylamido)-cephalosporanic acid β-S-oxide is obtained in the form of a beige solid.

TLC (eluant as in the preceeding example) Rf 0.22, IR in KBr: lactam CO at 1788 cm$^{-1}$.

NMR: thiazol protons at δ8.96 and 9.23 ppm ((CD$_3$)$_2$SO), each time doublets J=2 c.p.s.

Preparation of the starting compounds (a) 1,3-Thiazol-4-yl-glyoxylic acid ethyl ester A solution of 89.2 g of bromoacetylglyoxylic acid ethyl ester in 100 ml of ethanol is added dropwise at −10° C. to a solution of 30 g of thioformamide in 100 ml of ethanol. The mixture is stirred for 2 hours at 0° C., then for 2 hours without cooling with mild evolution of heat. Next, the reaction mixture is concentrated, methylene chloride is added, the precipitated crystalline product is removed, and the organic phase is concentrated and distilled in vacuo. The 1,3-thiazol-4-yl-glyoxylic acid ethyl ester passes over at 105° to 122° C. at 1 mm in the form of a weakly yellow oil.

Alternatively, the 1,3-thiazol-4-yl-glyoxyl ester is obtained by heating 17.1 g of 1,3-thiazol-4-yl-acetic acid ethyl ester in 50 ml of 1,2-dichloroethane together with 10.5 g of SeO$_2$ with reflux on a water separator. When the separation of water is complete, the mixture is filtered with suction, the residue is washed with 1,2-dichloroethane, the combined dichloroethane phases are concentrated and the residue is distilled.

(b) 1,3-Thiazol-4-yl-glyoxylic acid 18.5 g of the 1,3-thiazol-4-yl-glyoxylic ester are added to 60 ml of 2 N NaOH while cooling with ice. After 10 minutes, the mixture is warmed up for a short period of time, cooled again, filtered and the pH of the filtrate is adjusted to 3 by adding concentrated HCl. The solution is concentrated to dryness and digested with acetone. The solid obtained is isolated and washed with methanol and ether. 1,3-Thiazol-4-yl-glyoxylic acid is obtained in the form of a cream-colored solid melting at 185° to 190° C. with decomposition.

(c) 2-(1,3-thiazol-4-yl)-2-syn-methoximino-acetic acid 55 g of 1,3-thiazol-4-yl-glyoxylic acid ethyl ester are dissolved in 500 ml of glacial acetic acid at room temperature and, while stirring, a solution of 23.4 g of O-methylhydroxylamine hydrochloride in 100 ml of water is added. 30 g of sodium acetate are then added. The reaction mixture is stirred for 4 hours at room temperature and finally poured into 2 liters of water. The mixture is repeatedly extracted with chloroform. The combined organic phases are dried over MgSO$_4$ and concentrated to dryness.

The remaining oil is taken up in toluene, filtered over neutral Al$_2$O$_3$ and the eluate is concentrated again. 2-(1,3-Thiazol-4-yl)-2-syn-methoximino-acetic acid ethyl ester is obtained in the form of an oil, which is introduced, without further purification, into a solution of 130 ml of ethanol and 130 ml of 2 N NaOH. After heating on the steam bath for a short period of time, a pH of 5 is adjusted and the mixture is concentrated to dryness. The residue is taken up in 50 ml of water and a pH of 1.5 is adjusted with 2 N HCl, whereupon the product separates in crystal form. The crystals are isolated, washed with water and dried. 2-(1,3-Thiazol-4-yl)-2-syn-methoximino-acetic acid is obtained in the form of colorless crystals melting at 156° to 158° C. with decomposition. NMR [(CD$_3$)$_2$SO]: 9.2 ppm (d, aromatic H), 8.1 ppm (d, aromatic H), 4.0 ppm (s, O—CH$_3$).

Alternatively, the same compound can be prepared by admixing 20 g of 2-(1,3-thiazol-4-yl)-2-hydroximino-acetic acid ethyl ester (synthesis d), in 100 ml of acetone, with 27.6 g of K$_2$CO$_3$, adding 13.8 g of dimethyl sulfate at room temperature to the reaction mixture and, when the mild exothermal reaction is complete, heating the mixture to boiling for 1 hour. After cooling, the organic phase is isolated, the solvent is evaporated, and the residue taken up in chloroform and repeatedly washed with water. After separation of the phases, the organic phase is concentrated and the remaining oily 2-(1,3-thiazol-4-yl)-2-syn-methoximino-acetic acid ethyl ester is saponified in known manner to give 2-(1,3-thiazol-4-yl)-2-syn-methoximino-acetic acid, which is obtained in the form of colorless crystals melting at 156° to 159° C. with decomposition and is identical with the compound prepared by reacting 1,3-thiazol-4-yl-glyoxylic acid ester with O-methylhydroxyl amine.

(d) 2-(1,3-Thiazol-4-yl)-2-syn-hydroximino-acetic acid ethyl ester

A solution of 9 g of sodium acetate in 10 ml of water, and then a solution of 7.6 g of hydroxyl amine hydrochloride in 100 ml of water, are added to a solution of 18.5 g of 1,3-thiazol-4-yl-glyoxylic acid ethyl ester in 25 ml of glacial acetic acid. After a short standing at room temperature, crystals start to separate. After 2 hours, the reaction mixture is intensely cooled and the crystals are filtered off, washed with water and dried. 2-(1,3-Thiazol-4-yl)-2-syn-hydroximino-acetic acid ethyl ester is obtained in the form of colorless crystals melting at 175° to 178° C.

(3) 2-(1,3-Thiazol-4-yl)-2-syn-hydroximino-acetic acid

The crystals obtained sub (d) can be saponified without difficulty with 2 N NaOH at room temperature. After acidification to pH 2, filtration, washing with water and drying, 2-(1,3-thiazol-4-yl)-2-syn-hydroxylimino-acetic acid is obtained in the form of cream-colored crystals melting at 178° to 181° C. with decomposition.

(f) 2-(1,3-Thiazol-4-yl)-2-syn-triphenylmethoximino-acetic acid 3.3 g of triethyl amine and 8.35 g of triphenyl-chloromethane are added to a solution of 6 g of 2-(1,3-thiazol-4-yl)-2-syn-hydroximino-acetic acid ethyl ester in 75 ml of methylene chloride. The mixture is refluxed for 3 hours, cooled and washed with water. The organic phase is dried over MgSO₄. The solvent is distilled off and ether is added to the residue. The product obtained is isolated, washed with ether and dried, whereupon 2-(1,3-thiazol-4-yl)-2-syn-triphenylmethoximino-acetic acid ethyl ester is obtained as a solid melting at 130° to 134° C.

The ester obtained is heated for 2 hours on the steam bath in a mixture of 110 ml of 2 N NaOH and 110 ml of ethanol, left to stand for 16 hours at room temperature, cooled and acidified to pH 2 with 2 N HCl. The crystals formed are filtered off with suction, washed with water and dried in vacuo. 2-(1,3-Thiazol-4-yl)-2-syn-triphenylmethoximino-acetic acid melting at 160° to 163° C. with decomposition is isolated.

(g) 2-(1,3-Thiazol-4-yl)-2-syn-hydroximino-acetic acid ethyl ester 21.5 g of 2-(2-aminothiazol-4-yl)-2-syn-hydroximino-acetic acid ethyl ester are dissolved at −30° C. in 180 ml of hypophosphorus acid and 35 ml of nitric acid (d=1.4) and 13.8 g of sodium nitrite in 25 ml are slowly added. When the development of nitrogen is terminated, the mixture is allowed to warm up to room temperature, neutralized with soda (pH=4), diluted with about 100 ml of water and exhaustively extracted with ether. When concentrating the organic phase, the title compound remains behind in the form of a brownish oil which crystallizes on standing. Melting point 175° to 177° C. The acid is saponified as described sub (e).

(h) 2-(1,3-Thiazol-4-yl)-2-syn-methoximino-acetic acid ethyl ester (α) 22.9 g (0.1 mol) of 2-(2-aminothiazol-4-yl)-2-syn-methoximino-acetic acid ethyl ester are dissolved at −10° C. in 140 ml of phosphoric acid (d=1.7) and 40 ml of nitric acid (d=1.4) and then 13 g of sodium nitrite in 20 ml of water are added dropwise while stirring. Next, the reaction mixture is added dropwise and at −5° C. to a mixture of 310 ml of hypophosphorus acid ($H_3PO_2$) and 14 g of pulverulent copper. When the development of nitrogen is terminated (about 30 minutes), the mixture is neutralized with soda and repeatedly extracted with ether. The dried organic phase is evaporated, whereupon the 2-syn-methoximino-2-thiazol-4-yl-acetic acid ethyl ester is obtained in the form of a yellowish oil which can be converted by alkaline saponification, without further purification, into the acid.

Rf-value (SiO₂/ether) 0.57.
NMR: [(CD₃)₂SO]
9.2 ppm (S, aromatic H)
8.1 ppm (s, aromatic H)
4.1–4.5 ppm (q, —CH₂-ester)
4.0 ppm (s, —OCH₃)
1.2–1.4 ppm (t, CH₃-ester)

(β) 2-(2-Bromo-thiazol-4-yl)-2-syn-methoximino-acetic acid ethyl ester 22.9 g (0.1) of 2-(2-amino-thiazol-4-yl)-2-syn-methoximino-acetic acid ethyl ester are dissolved at −10° C. in 140 ml of phosphoric acid (d=1.7) and, while stirring, 40 ml of nitric acid (d=1.4) and then 13 g of sodium nitrite in 20 cc of water are added dropwise. The reaction mixture is added dropwise at −50° C. to a mixture of 310 ml of 48% hydrobromic acid and 14 g of pulverulent copper. When the development of nitrogen is terminated, the mixture is neutralized with soda, diluted with water and extracted 4 times, each time with 500 ml of ether. After removal of the solvent and vacuum distillation (0.4 mm/114° C.), 2-(2-bromo-thiazol-4-yl)-2-syn-methoximino-acetic acid ethyl ester is obtained from the dried organic phase.

The position of the aromatic proton of the thiazol ring at 7.5 ppm (CDCl₃) and of the —OCH₃-group at 4.0 ppm are characteristic for the syn-configuration of the methoximino group.

The signals of these groups in the anti-compound are, correspondingly, at 8.1 ppm and 4.1 ppm.

5.8 g (0.02 mol) of 2-(2-bromo-thiazol-4-yl)-2-syn-methoximino-acetic acid ethyl ester are dissolved in 75 ml of ethanol, 3 g of diethyl amine are added and the mixture is hydrogenated with Raney nickel at atmospheric pressure. After about ½ hour, the theoretical amount of hydrogen is consumed. The catalyst is cautiously filtered off with suction, the solvent is removed and, by a treatment with ether, the 2-(1,3-thiazol-4-yl)-2-syn-methoximino-acetic acid ethyl ester is separated from the diethyl amine hydrobromide.

What is claimed is:

1. A cephalosporin compound selected from the group consisting of (a) compounds of the formula wherein n is 0 or 1, A is methyl or —CH₂O-acyl where acyl is alkanoyl having 1 to 5 carbon atoms, Z is oxygen or =NOR wherein R is hydrogen or saturated or unsaturated aliphatic hydrocarbon having up to five carbon atoms, and R¹ is hydrogen or lower alkoxy;

(b) pharmaceutically acceptable salts thereof; and (c) phthalide esters, lower alkyl esters, and substituted methyl esters thereof wherein the methyl group is mono-substituted by trichloromethyl or alkanoyloxy having 2 to 5 carbon atoms, or is mono- or di-substituted by phenyl or by phenyl in turn substituted by lower alkoxy or nitro.

2. A compound as in claim 1 which is 7-[2-(1,3-thiazol-4-yl)-2-syn-methoximino-acetamido]-cephalosporanic acid.

3. A pharmaceutical composition for combatting bacterial infections, which composition comprises an antibacterially-effective amount of a compound as in claim 1 together with a pharmaceutically acceptable carrier therefor.

4. A method for combatting a bacterial infection in a patient suffering therefrom, which method comprises parenterally or orally administering to said patient an antibacterially-effective amount of a compound as in claim 1.

5. A cephalosporin compound as in claim 1 wherein Z is oxygen.

6. A cephalosporin compound as in claim 1 wherein n is 1.

7. A cephalosporin compound as in claim 1 wherein Z is oxygen and n is 1.

* * * * *